US012708295B2

(12) United States Patent
Borremans et al.

(10) Patent No.: US 12,708,295 B2
(45) Date of Patent: Aug. 18, 2026

(54) SELECTABLE ENERGY MODES FOR MEASURING BLOOD AND TISSUE OXYGENATION

(71) Applicant: Spectricity, Mechelen (BE)

(72) Inventors: Jonathan Borremans, Lier (BE); Ward van der Tempel, Keerbergen (BE); Jakub Raczkowski, Bertem (BE)

(73) Assignee: Spectricity, Mechelen (BE)

( * ) Notice: Subject to any disclaimer, the term of this patent is extended or adjusted under 35 U.S.C. 154(b) by 535 days.

(21) Appl. No.: 18/313,739

(22) Filed: May 8, 2023

(65) Prior Publication Data

US 2023/0270360 A1 Aug. 31, 2023

Related U.S. Application Data

(63) Continuation of application No. PCT/US2021/072619, filed on Nov. 29, 2021.

(60) Provisional application No. 63/119,386, filed on Nov. 30, 2020.

(51) Int. Cl.
*A61B 5/1455* (2006.01)
*A61B 5/00* (2006.01)

(52) U.S. Cl.
CPC ........ *A61B 5/14551* (2013.01); *A61B 5/0075* (2013.01)

(58) Field of Classification Search
CPC .................................................... A61B 5/1455
See application file for complete search history.

(56) References Cited

U.S. PATENT DOCUMENTS

| | | | |
|---|---|---|---|
| 10,568,525 | B1 | 2/2020 | Wu et al. |
| 2020/0237317 | A1 | 7/2020 | Newberry et al. |
| 2020/0297221 | A1 | 9/2020 | Hirano et al. |

FOREIGN PATENT DOCUMENTS

| | | |
|---|---|---|
| JP | 2016101393 A | 6/2016 |
| WO | 2019141869 A1 | 7/2019 |

OTHER PUBLICATIONS

International Searching Authority; International Search Report and Written Opinion; International Application No. PCT/US2021/072619; Mar. 21, 2022; 13 pgs.

*Primary Examiner* — Marjan Fardanesh
(74) *Attorney, Agent, or Firm* — Katz Ruby & Carle LLP; Kelly H. Hale

(57) ABSTRACT

A method for measuring body parameters includes irradiating a body area during a first time window using a first illumination source of a predetermined range of optical wavelengths and sampling, by a first plurality of spectral sensors, a first received light spectrum for the body area. The method continues by outputting, via one or more interfaces, information representative of the first received light spectrum during the first time window to a processor. The method continues by irradiating the body area during a second time window using a second illumination source of a predetermined range of optical wavelengths and sampling, by a second plurality of spectral sensors, a second received light spectrum for the body area. The method continues by outputting, via the one or more interfaces, information representative of the second received light spectrum during the first time window to the processor.

22 Claims, 11 Drawing Sheets

SELECTABLE ENERGY MODES FOR MEASURING BLOOD AND TISSUE OXYGENATION

CROSS-REFERENCE TO RELATED APPLICATIONS

The present application claims priority claims priority pursuant to 35 U.S.C. § 120 and 35 U.S.C. § 365(c) as a continuation of International Application Number PCT/US2021/072619, entitled "SELECTABLE ENERGY MODES FOR BLOOD AND TISSUE OXYGENATION MEASUREMENT", filed Nov. 29, 2021, which claims priority pursuant to 35 U.S.C. § 119(e) to U.S. Provisional Patent Application No. 63/119,386, entitled "SELECTABLE ENERGY MODES FOR BLOOD AND TISSUE OXYGENATION MEASUREMENT", filed Nov. 30, 2020, both of which are incorporated herein by reference in their entirety and made part of the present application for all purposes.

BACKGROUND OF THE INVENTION

Technical Field of the Invention

This invention relates generally to blood oxygenation measurement and more particularly to variable energy modes for blood oxygenation measurement.

Spectroscopy devices have proven to be useful for applications in various industries including, for example, health, biometrics, agriculture, chemistry and fitness. Spectroscopy involves the measurement of spectra produced when matter interacts with or emits electromagnetic radiation. A light source penetrates material based on the components of the light source and the properties of the material and its spectral components are captured by a detector as a combination of propagated, scattered and transmitted light that can reveal attributes of the material.

Blood and tissue oxygenation ($SO_2$) are important parameters in health assessment. Oxygen saturation in blood and tissue can be measured using optical measurements of light absorption in various optical wavelengths using various techniques, such as oximetry. Oximetry is a technique for the assessment of blood oxygenation that measures light transmission through blood, which depends on the absorption spectra of oxygenated (HbO2) and deoxygenated (dHb) hemoglobin.

Portable oximetry devices can suffer a trade-off between accuracy and energy consumption. Increasing the number of wavelengths used in blood oxygen determination can improve the accuracy of the $SO_2$ measurement, however, spectrometry can be less power efficient than traditional techniques. Moreover, the sensitivity of the hyperspectral receivers can also be lower than traditional methods.

DESCRIPTION OF RELATED ART

Brief Description of the Several Views of the Drawing(s)

FIG. 1 illustrates the various blood oxygen components measured with an example oximetry device;

FIG. 2 provides a graph illustrating the absorption profiles of oxygenated ($HbO_2$) and deoxygenated blood (dHb);

DETAILED DESCRIPTION OF THE INVENTION

In various embodiments, spectral sensors are combined with traditional blood oximetry techniques to provide spectral information about the health, fitness and safety of blood and tissue. In general, the transmission of light through a given tissue depends on the light absorption and the light scattering coefficients of arterial and venous blood and of the various components of tissue being measured. Diffuse optical reflectance spectroscopy involves illuminating a material and detecting light propagated from the material being illuminated, while transmittance spectroscopy involves the capture of light transmitted through a material to the detector. The contribution of the blood to the light absorption and light scattering can be isolated by using light sources of various wavelengths and by isolating the contribution of blood to the light absorption using photoplethysmography (PPG) which involves the measurement of light absorption changes due to the cardiac induced blood volume changes. In an example, pulse oximetry enables the assessment of the oxygen saturation based on PPG signals derived from arterial blood volume increase during systole, by measuring the PPG signal in multiple wavelengths.

In some embodiments, small-scale spectral imaging systems for oximetry can be adapted for use in mobile devices. Examples of mobile devices include, but are not limited to, smart mobile phones, smart watches, skin patches, medical probes and crowd-sourced monitoring devices.

Figure 1:
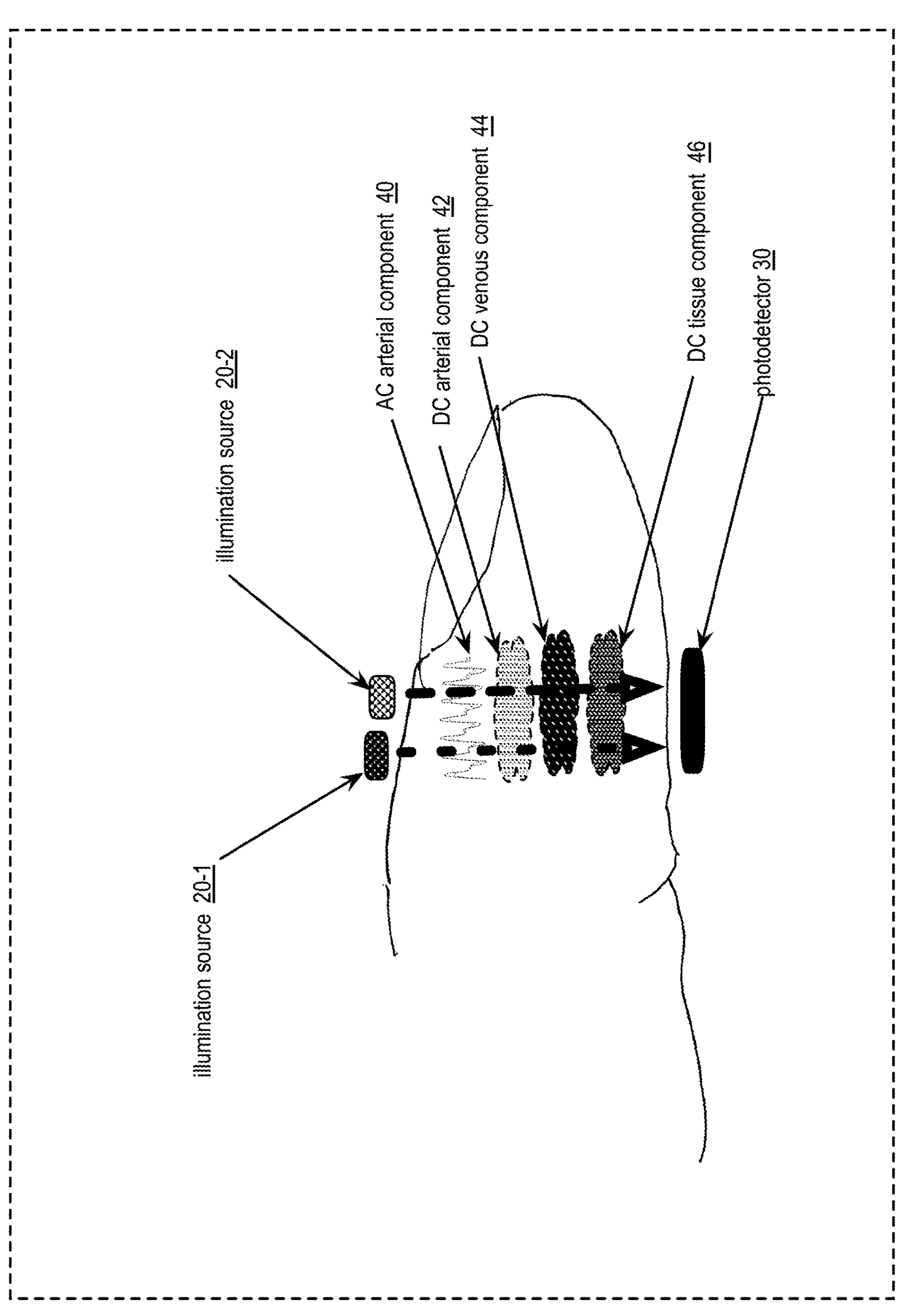

FIG. 1 illustrates the various blood oxygen components that can be measured using an example oximetry device. As discussed above, a photoplethysmogram (PPG), is an optically obtained plethysmogram useful for detecting blood volume changes in a microvascular bed of tissue, such as the finger illustrate in FIG. 1. In an example, the change in blood volume results in a change in the intensity of transmitted light from illumination source 20-1 and illumination source 20-2 through finger tissue to photodetector 30. In an example, a PPG has two basic components: a non-pulsatile (DC) and a pulsatile (AC) component of body light absorption. The DC component contains information of the blood present in the tissue and from scattering produced by the tissue and bones (DC tissue component 46), veins (DC venous component 44) and a DC arterial component 42 (arterial blood remaining in the artery during diastole). The AC arterial component 40 provides information representative of the blood in the arteries because it derives from the effect of pulsation during heart beats, whereas the DC components are minimally affected by heart pulsation.

The relative response of the AC arterial component 40 of a PPG can be shown to be in the range of less than 0.1% to more than 2% of the signal received at photodetector 30, whereas the DC components are responsible for less than 98% to more than 99.9% of the signal received. Said another way, 2% of the absorption of light passing through the finger illustrated in FIG. 1 is from AC arterial component 40, while the other 98% of the absorption can be from a combination of the DC tissue component 46, DC venous component 44 and the DC arterial component 42.

Figure 2:
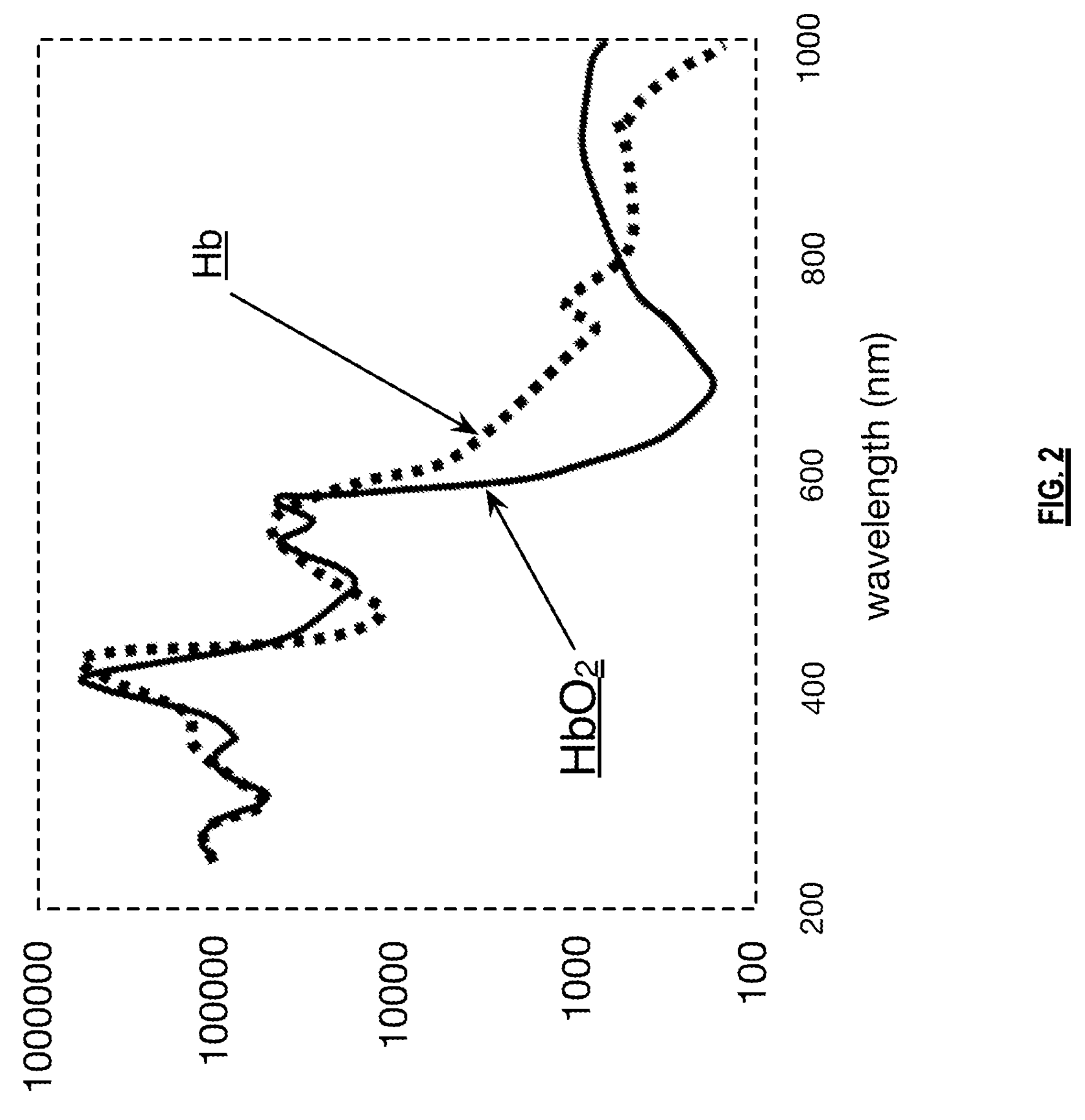

Analysis of the AC arterial component 40 component of a PPG can be used to measure the arterial oxygen saturation ($SpO_2$). In the analysis the amplitude of the AC signal can be a critical extraction parameter in a pulse oximetry system. Absorption in blood can be shown to be dependent on two main contributors: oxygenated ($HbO_2$) and deoxygenated (dHb) hemoglobin. FIG. 2 provides a graph illustrating the absorption of oxygenated ($HbO_2$) and deoxygenated blood (dHb) for the full spectral range between 200 nm and 1000 nm.

An example formula for computing $SpO_2$ from the two signal is (where the illumination sources 20-1 and 20-2 are 660 nm and 940 nm, respectively):

$$R = \frac{AC660/DC660}{AC940/DC940}$$

In the example, R is directly proportional to $SpO_2$ with a scaling factor. The quality of the computation of the AC component (such as AC arterial component 40) can be critical as it can directly represent $SpO_2$ output. Measuring and calculating the AC component, which is generally a small, time-varying signal, can be complex, as illustrated below in FIG. 3.

Figure 3:
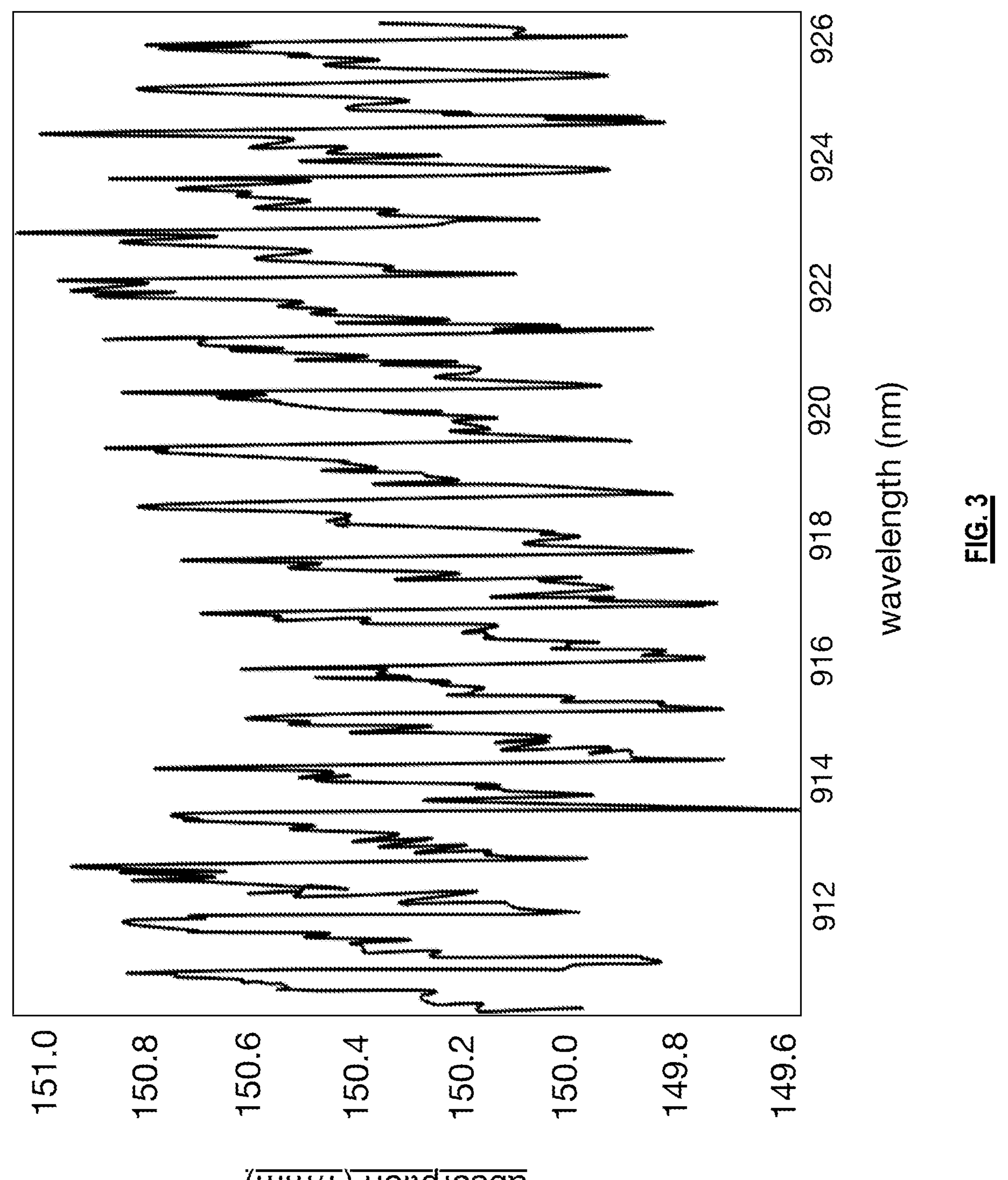
FIG. 3 illustrates the time-varying contribution of the AC component in a representative oximetry system.

FIG. 3 illustrates the time-varying contribution of the AC component (such as AC arterial component 40), in a representative oximetry system with the abscissa (horizontal axis) shown in seconds, with the ordinate (vertical axis) expressed as a molar extinction coefficient (cm-1/M), which can be considered as a measure of how strongly a chemical species or substance absorbs light at a particular wavelength. Amplitude extraction of the AC component can be done in several ways, including the use of a time-based algorithm for extracting the local maxima and minima (peaks and valleys) in the signal. Additional methods include a fast-fourier transform (FFT) based analysis for determining the amplitude and frequency of the AC component, as well as even more complex methods.

Figure 4:
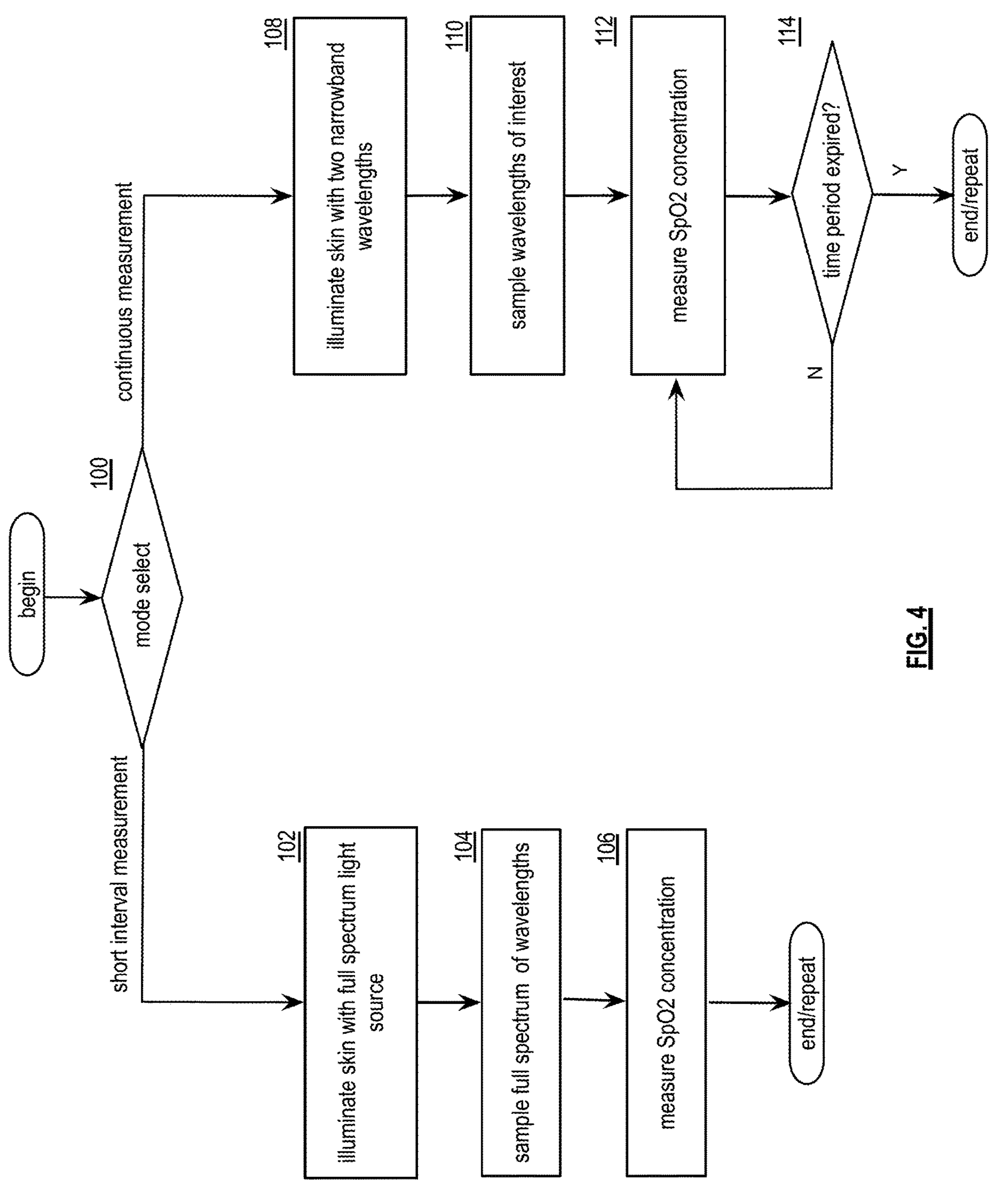
FIG. 4 is a flowchart of a method incorporating a spectrometer for measuring $SpO_2$ with two operation modes in accordance with the present invention.

FIG. 4 is a flowchart of a method incorporating a spectrometer for measuring $SpO_2$ with two operation modes. At step 100, a mode selection is made between two operational modes. When continuous measurement is selected, the skin is illuminated at step 108 using two narrowband wavelengths, such as the illumination sources illustrated in FIG. 1. In an example of implementation, narrow-band light emitting diodes (LEDs) can be used. In a related example, the narrow-band LEDs can be highly efficient illumination sources optimized for power consumption. The method continues at step 110, where the wavelengths of interest are sampled. In a specific example of operation, a spectrometer can be adapted to limit sampling the signals to the wavelength bands of interest. In another specific example, the sampling is done using one or more photodetectors, such as photodetector 30 from FIG. 1. In an example of implementation and operation, a system operating in this mode can have an average current consumption of ~1 mA. An example use case is sleep apnea detection where accuracy of $SpO_2$ is not as critical, while relative $SpO_2$ is of interest.

At step 112 $SpO_2$ is determined/measured based on the sampled wavelengths. The method then continues at step 114, where an optional timer can be used to determine whether a time window has expired, and when the time window has not expired, the $SpO_2$ concentration is measured until the time window is met or exceeded. In a specific example, the $SpO_2$ concentration is determined/measured based on a duty cycle, where a duty cycle (%) is expressed as:

$$D = PW/T^{*}\ 100\% \text{ or}$$

In another example the duty cycle can be expressed as a ratio where:

$$D = PW/T$$

In the examples incorporating duty cycles, D is the duty cycle, PW is the pulse width (pulse active time) for driving the illumination sources and/or spectrometer (or photodetector), and T is the total time window for the signal. Thus, a 60% duty cycle means the signal is on 60% of the time but off 40% of the time. The "on time" for a 60% duty cycle could be a fraction of a second, a day, or even a week, depending on the length of the period. In another specific example, the $SpO_2$ concentration is measured on a relatively continuous basis when continuous measurement is selected. In yet another specific example (not shown), the duty cycle is also used at the illuminating at step 108 and/or sampling of step 110 is based on the duty cycle triggers $SpO_2$ measurement. In another specific example, the illumination step 108 can commence before the sampling and/or measurement steps 110 and 112 respectively, such that a skin area being analyzed is illuminated prior to sampling and/or measurement.

When short interval measurement (spot measurement) is selected at step 100, skin is illuminated at step 102 with a broad or full spectrum light source. In an example of implementation, one or more full wide-band light emitting diodes (LEDs) can be used. In another example, the broad-spectrum light source can comprise a plurality of LEDs over a broad wavelength distribution. In an example, the full spectrum light source will require high current consumption but could be selected for relatively short periods of time during a given time window. In a specific example, the full spectrum illumination source can be used for measurements of a minute or less for a limited number of times per time window, where the time window can be, for example, a day. The method continues at step 104 with a spectrometer being used to sample the full spectrum of wavelengths and continues at step 106, with $SpO_2$ concentration being determined/measured based on the sampled wavelengths. In an example the short illumination mode may be a spot measurement where high-accuracy $SpO_2$ matters, such as a spot measurement for respiratory diseases.

In an example of operation, mode select 100 can be implemented according to a duty cycle, such as discussed above, with the mode select 100 selecting a short interval measurement using full spectrum light, along with full spectrum measurement and $SpO_2$ measurement for short periods during a given time window. In an example, the short interval measurement can consume high current, such as 10 mA during a 15 second measurement, without having high aggregate power consumption. In another specific example, the short interval measurement is implemented using a very low duty cycle ratio, with the continuous measurement utilizing a much higher duty cycle ratio or running continuously. In a related specific example, the selection of short interval measurement can trigger illumination for a predetermined time interval before the sample and measurements, respectively, of steps 104 and 106 are executed, such that the sample and/or measurement takes place after the skin has been fully illuminated and the full spectrum illumination source(s) have stabilized.

In a specific example of implementation and operation, a method for measuring spectrophotometric parameters of a body area (such as skin), includes irradiating the body area during a first time window, by a first illumination source, where the first illumination source is configured to provide light over a predetermined range of optical wavelengths and where the first illumination source is further configured to irradiate light directly onto the body area. In a specific example, the predetermined range of optical wavelengths for the first illumination source is between 930 nm and 950 nm. In another example of implementation, the first time window is based on a first duty cycle, wherein a duty cycle is a fraction of time in a time window during which an illumination source is emitting light. The method continues by sampling a first received light spectrum from one or more spectrometers during the first time window, where each of the one or more spectrometers includes a plurality of interference filters overlaying one or more optical sensors and where each of the one or more spectrometers has a sensing range within a predetermined range of optical wavelengths and is configured to capture light emitted from the body area and where each of the one or more spectrometers is positioned a predetermined distance from at least one illumination source of the one or more illumination sources. In a specific example, a processor is coupled to the one or more spectrometers and is adapted to limit the sensing range of the one or more spectrometers to wavelengths associated with the first illumination source.

The method continues by irradiating the body area, by a second illumination source, where the second illumination source is configured to provide light over a predetermined range of optical wavelengths and where the second illumination source is also configured to irradiate light directly onto the body area. In a specific example, the second and first illumination sources are configured to illuminate in relatively the same time window. In an alternative example, the second illumination source is configured to partially overlap the illumination by the first illumination source or even in a second time window that is distinct from the first time window. In a specific example, the predetermined range of optical wavelengths for the second illumination source is between 640 nm and 680 nm. In another example of implementation, the second time window is based on the first duty cycle, and in another example, the second time window is based on a second duty cycle, that is associated with the first duty cycle. The method then includes sampling a second received light spectrum from the one or more spectrometers during the second time window. In a specific example, the processor is further adapted to limit the sensing range of the one or more spectrometers to wavelengths associated with the second illumination source.

At a next step the method continues by irradiating the body area during a third time window, by a third illumination source, where the third illumination source is configured to provide light over a predetermined range of optical wavelengths and where the third illumination source is further configured to irradiate light directly onto the body area and sampling a third received light spectrum from the one or more spectrometers during the third time window. In an example, the predetermined range of optical wavelengths for the third illumination source is broader than the predetermined range of optical wavelengths for the first illumination source and second illumination source. In a specific related example, a processor is adapted to use the full sensing range of the one or more spectrometers to provide full spectrum sampling of the light transmitted and scattered from the third illumination source. In a specific example, the predetermined range of optical wavelengths for the third illumination source is a range in between 400 nm and 1000 nm. In another example of implementation, the third time window is based on a third duty cycle that is significantly shorter than either the first or the second duty cycles for the first and second illumination sources.

The method concludes with the processor determining one or more blood oxygenation ($SO_2$) parameters based on (indicated by) the first, second and the third received light spectrum. In a specific example, the blood oxygenation ($SO_2$) parameters can include peripheral oxygen saturation ($SpO_2$), venous oxygenation saturation ($SvO_2$), and tissue oxygenation saturation ($StO_2$).

In a specific example of application, blood oxygenation ($SpO_2$) can be helpful for the treatment, analysis and diagnosis of health conditions. For example, chronic obstructive pulmonary disease (COPD) is a long-term lung condition that can make it difficult for a person to breath, thus monitoring $SpO_2$ is an important addition to treatment protocols. Other examples where benefit is derived from monitoring $SpO_2$ parameters include treatment of asthma, chronic bronchitis, diseases that include respiratory complications, such as COVID-19. The diagnosis of other health issues, such as sleep conditions like sleep apnea and narcolepsy and exercise related conditions can also be aided with careful $SpO_2$ monitoring.

With these and other health and exercise conditions, the type and quality requirements for $SpO_2$ measurements can be diverse. For example, in some cases, such as those where $SpO_2$ varies slowly, only a few measurements are need over a relatively long period of time, however high accuracy will be required for those measurements. In an example, 3% absolute accuracy is important. In other cases, such as in the diagnosis and analysis of sleep apnea, $SpO_2$ is preferably measured on a relatively constant basis, with the number and timing of "dips" being important. For example, short drops in $SpO_2$ such as a minute or less are preferably measured and tracked, while the amount of drop may not be so important. In this example, the relative $SpO_2$ measurement accuracy requirement can be important, (such as, for example, 3%) while absolute accuracy can be lower without a significant effect on diagnosis and/or treatment.

In other examples, $SpO_2$ needs to be measured on a relatively constant basis in order to identify an event, which can be used to trigger highly accurate measurements of the $SpO_2$ during an event and even after the event. Additionally, oximetry devices used for most oximetry applications routinely benefit from being small and battery operated, so as to be less intrusive and/or less costly. In an example, wideband illumination sources for oximetry can provide exceptionally accurate and precise oximetry measurements, however the inefficiency of such illumination sources render them unfeasible for use in continuous measurements, whereas two-band narrow wavelength sources can be much more efficient but suffer from markedly lower accuracy and/or precision. Other factors can also be important. For example, prolonged exposure to wideband illumination sources can be damaging to some types of tissues and for some patients, such as infants being treated resulting from preterm birth (preemies). In a specific related example, hyperoxygenation in a preemie can result in severe health problems relating to eyes (retinopathy) and brain health, due to fetal hemoglobin (Hbf) having higher affinity for oxygen than that of normal adult Hb, even though a same level of oxygenation would be relatively harmless to a normal newborn. Thus, high precision and accuracy may be required along with continuous monitoring, all-the-while being mobile and efficient.

In other examples, such as, for example during hyperbaric oxygen therapy (especially when a patient requires mechanical ventilation) accurate and precise monitoring of $SpO_2$ can provide better treatment outcomes, however limited space and other factors can limit traditional monitoring devices. Accordingly, as with the applications discussed above, a system with two-modes of operation can provide many or all of the benefits of both wide-band and narrow band illumination while retaining mobility, power efficiency and a small form factor.

In a specific example of implementation and operation, a method for measuring body parameters includes irradiating a body area during a first time window using a first illumination source, where the first illumination source is configured to provide light over a predetermined range of optical wavelengths and is configured to irradiate light directly onto the body area. The method continues by sampling, by a first plurality of spectral sensors, a first received light spectrum for the body area, where each spectral sensor of the first plurality of spectral sensors includes a spectral filter overlaying an optical sensor, where each spectral sensor has a sensing range within a predetermined range of optical wavelengths, where the sensing range for the first plurality of spectral sensors includes a spectrum of wavelengths and wherein each spectral sensor is positioned a predetermined distance from the first illumination source. The method then continues by outputting, via one or more interfaces, information representative of the first received light spectrum during the first time window to a processor or processors. The method continues by irradiating the body area during a second time window using a second illumination source, where the second illumination source is configured to provide light over a predetermined range of optical wavelengths, where the second illumination source is configured to irradiate light directly onto the body area. The method then continues by sampling, by a second plurality of spectral sensors, a second received light spectrum for the body area, where each spectral sensor of the second plurality of spectral sensors includes a spectral filter overlaying an optical sensor, where each spectral sensor has a sensing range within a predetermined range of optical wavelengths, where the sensing range for the second plurality of spectral sensors includes a spectrum of wavelengths and where each spectral sensor is positioned a predetermined distance from the second illumination source a second received light spectrum from the one or more spectrometers during the second time window and then outputting, via one or more interfaces, information representative of the first received light spectrum during the first time window to the one or more processing modules.

Figure 5:
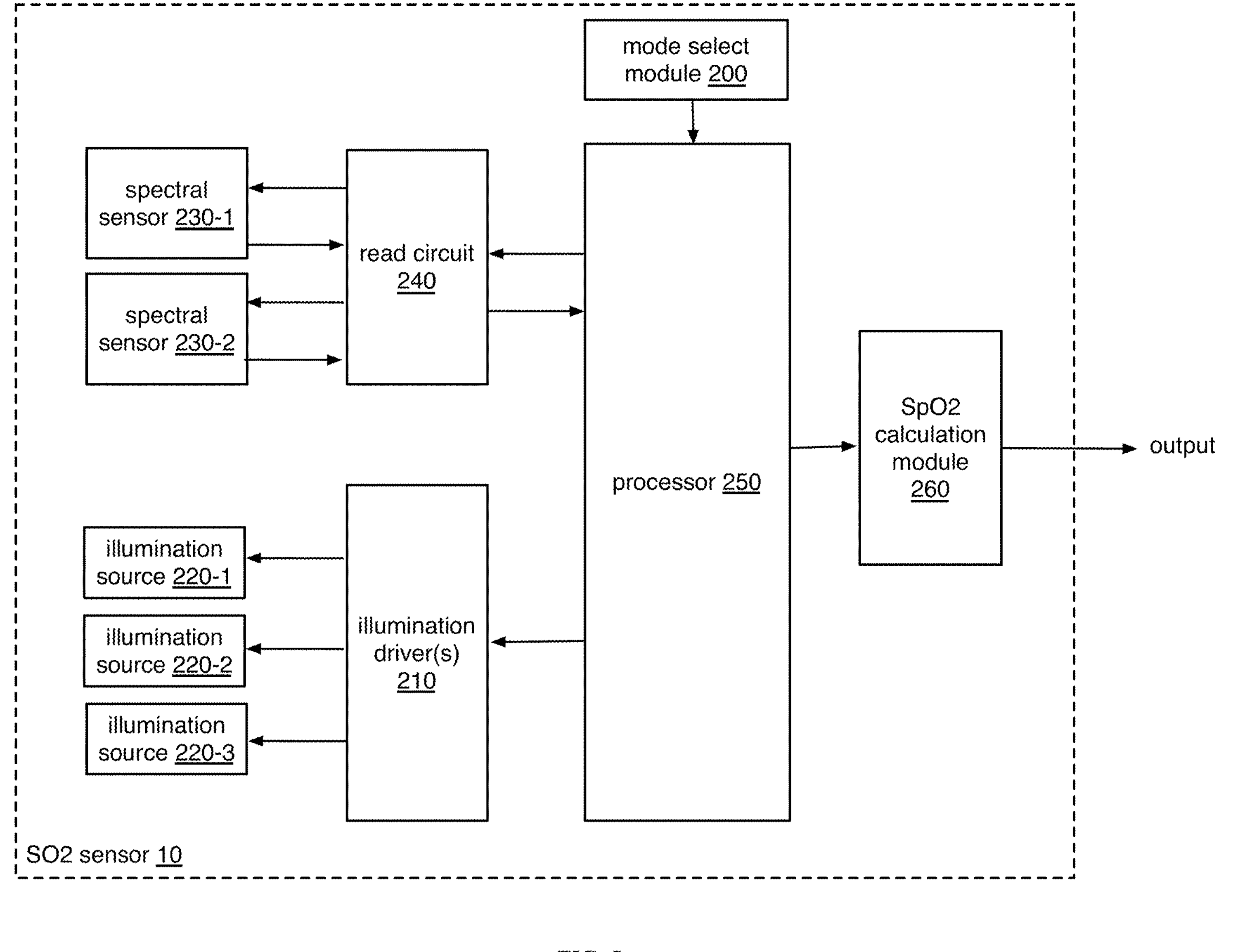
FIG. 5 is a schematic representation of an example narrowband/full band system for measuring $SpO_2$ in accordance with the present invention.

FIG. 5 is a schematic representation of an example narrowband/full band system for measuring $SpO_2$. In the example, a processor 250 is coupled to mode select module 200 and illumination driver(s) 210, read circuit 240 and $SpO_2$ calculation module 260. In an alternative example, mode select module 200 and or $SpO_2$ calculation module 260 are modules within processor 250. In an example, mode select module 200 is responsive to a timing element and/or manual implementation and upon selection the processor controls illumination driver(s) 210 accordingly. Illumination driver (s) 210 are coupled to illumination sources 220-1, 220-2 and 220-3. In a specific example, illumination source 220-1 and illumination source 220-2 are narrowband illumination sources, such as the 660 nm and 940 nm illumination sources illustrated in FIG. 2, while illumination source 220-3 is a broad-band illumination source. In a specific related example, illumination source 220-3 can comprise a plurality of LED light sources constituting a broad-band illumination spectrum together, or in another example, a single LED light source can provide the full spectrum of light.

Spectral sensor 230-1 receives the transmitted and scattered light from illumination sources 220-1, 220-2 and 220-3 and transmits the sampled signals to read circuit 240, which are then transmitted by the coupled processor 250 to the $SpO_2$ calculation module 260. In an example, an additional spectral sensor 230-2 is included and in yet another example, (not shown) one or more photodetectors are used instead of spectral sensor 230-2. In a specific example of implementation, processor 250 is also coupled to spectral sensor 230-1, so that when continuous monitoring is selected by mode select module 200 the processor can limit the sample wavelengths for spectral sensor to 230-1 to the wavelengths of interest, based on narrow-band illumination sources 220-1 and 220-2.

In a specific example of implementation, A device for measuring optical response from skin includes a first illumination source, where the first illumination source is configured to provide light over a predetermined range of optical wavelengths and is configured to irradiate light directly onto the skin. A second illumination source is included, where the second illumination source is configured to provide light over a predetermined range of optical wavelengths and is also configured to irradiate light directly onto the skin. In the example, a plurality of spectral sensors is included, where each spectral sensor of the plurality of spectral sensors includes a spectral filter overlaying an optical sensor, where each spectral sensor has a sensing range within a predetermined range of optical wavelengths, where the sensing range for the plurality of spectral sensors includes a spectrum of wavelengths and where each of the one or more spectrometers is positioned a predetermined distance from the first illumination source and the second illumination source.

a first module of the one or more processors is adapted to select between the first and second illumination sources and a second module of the one or more processors adapted to produce a spectral response from at least an associated subset of the plurality of spectral sensors for each of the first illumination source and the second illumination source.

Figure 6:
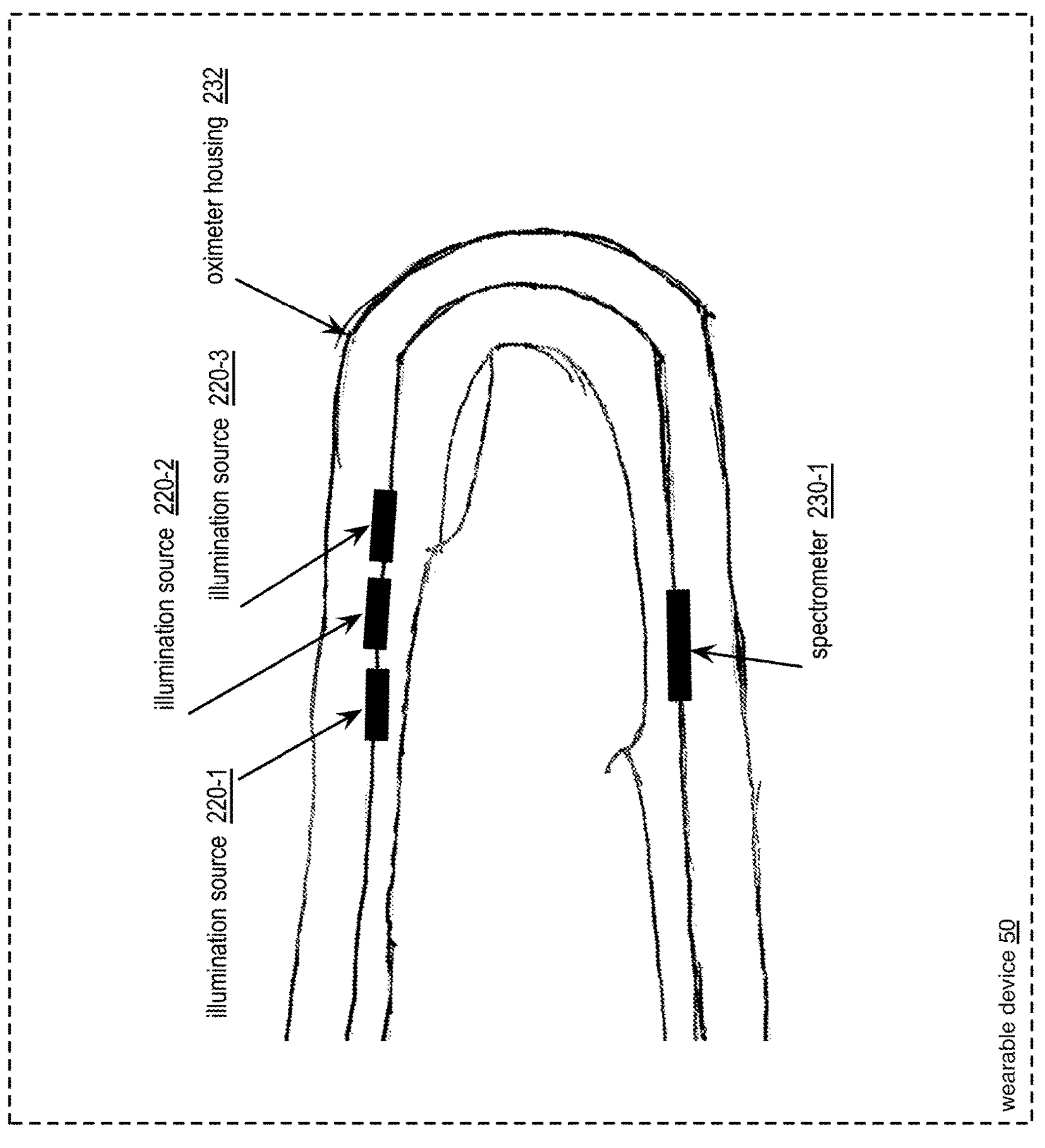
FIG. 6 illustrates an example implementation of narrowband/full band system for measuring $SpO_2$ in a finger oximeter in accordance with the present invention.

FIG. 6 illustrates an example implementation of narrowband/full band system for measuring $SpO_2$ in a finger oximeter. In the example, illumination sources 220-1 and 220-2 provide narrowband illumination through the finger, with transmitted and scattered light being received at spectrometer 230-1. In the example, the illumination sources and spectrometer 230-1 are contained in an oximeter housing 232 that is part of wearable device 50. In an example, the wearable device 50 also includes the elements of the narrowband/full band system of FIG. 5.

In a specific example of implementation and operation, A device for measuring optical response from skin includes a first illumination source, where the first illumination source is configured to provide light over a predetermined range of optical wavelengths and where the first illumination source is further configured to irradiate light directly onto skin. A second illumination source is included, where the second illumination source is configured to provide light over a predetermined range of optical wavelengths and where the second illumination source is also configured to irradiate light directly onto skin. In a specific example, the predetermined range of optical wavelengths for the second illumination source is between 640 nm and 680 nm.

A third illumination source is configured to provide light over a predetermined range of optical wavelengths, where the third illumination source is also configured to irradiate light directly onto skin. In an example, the predetermined range of optical wavelengths for the third illumination source is broader than the predetermined range of optical wavelengths for either of the first illumination source or the second illumination source. In a specific example, the predetermined range of optical wavelengths for the first illumination source is between 930 nm and 950 nm. In an example, the predetermined range of optical wavelengths for the first illumination source and the second illumination sources is narrower than the predetermined range of optical wavelengths for the third illumination source.

In an example, the device includes one or more spectrometers, wherein each of the one or more spectrometers includes a plurality of interference filters overlaying one or more optical sensors, where each of the one or more spectrometers has a sensing range within a predetermined range of optical wavelengths and is configured to capture light emitted from the skin and where each of the one or more spectrometers is positioned a predetermined distance from the first illumination source and the second illumination source. In the example, a first module of one or more processors, is adapted to select between one or more of the first, second and third illumination sources to illuminate the skin and a second module of one or more processors and a second module is adapted to produce a spectral response for at least a portion of one spectrometer of the one or more spectrometers.

In a specific example of implementation, the first module is adapted to select between the second and third illumination sources based on a first duty cycle, where a duty cycle is a fraction of time in a time window during which an illumination source is emitting light. In another example, the first module is also adapted to select the first illumination source based on a second duty cycle, where the second duty cycle is longer than the duty cycle for second illumination sources. In a specific example, the second duty cycle is in the range of minutes per day, while the first duty cycle can be as short as fractions of a second.

In a specific example of implementation and operation, a device for measuring optical response from skin includes a first illumination source, where the first illumination source is configured to provide light over a predetermined range of optical wavelengths and where the first illumination source is further configured to irradiate light onto skin. In the example, a second illumination source, is configured to provide light over a predetermined range of optical wavelengths, wherein the second illumination source is further configured to irradiate light onto skin. A third illumination source is configured to provide light over a predetermined range of optical wavelengths, where the third illumination source is further configured to irradiate light onto skin.

In an example, one or more spectrometers is included, where each of the one or more spectrometers includes a plurality of interference filters overlaying one or more optical sensors, where each of the one or more spectrometers has a sensing range within a predetermined range of optical wavelengths and is configured to capture light emitted from the skin. In an example, each of the one or more spectrometers is positioned a predetermined distance from the first illumination source, the second illumination source and the third illumination source and the one or more spectrometers are adapted to output, via an included interface (or interfaces) to one or more processors, where a first module of the one or more processors is adapted to select between one or more of the first, second and third illumination source to illuminate the skin and a second module of the one or more processors is adapted to produce a spectral response for at least a portion of one spectrometer of the one or more spectrometers.

Figure 7:
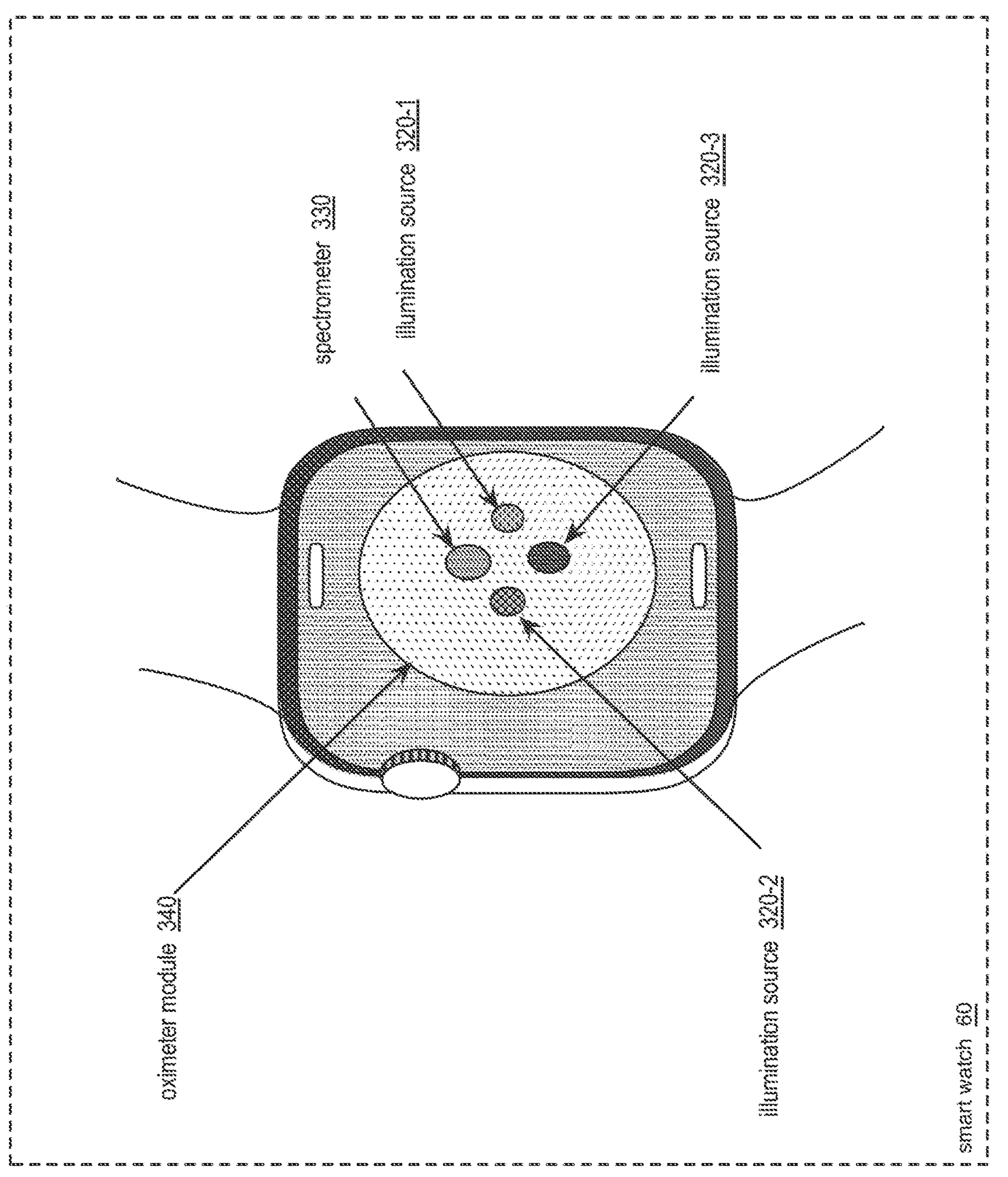
FIG. 7 illustrates an example implementation of narrowband/full band system for measuring $SpO_2$ in a smart watch in accordance with the present invention.

FIG. 7 illustrates an example implementation of narrowband/full band system for measuring $SpO_2$ in a smart watch. In the example, illumination sources 320-1 and 320-2 provide narrowband illumination to the skin under the backside of the smart watch 60, with transmitted and/or scattered light being received at spectrometer 330-1. In the example, the illumination sources and spectrometer 330-1 are contained in an oximeter module 340 that is part of smart watch 60. In an example, the smart watch includes the elements of the narrowband/full band system of FIG. 5. In an example, smart watch 60 is a fitness monitoring band, while in an alternative example smart watch 50 includes other functions, where $SpO_2$ monitoring is one of a multitude of smart watch functions.

Figure 8:
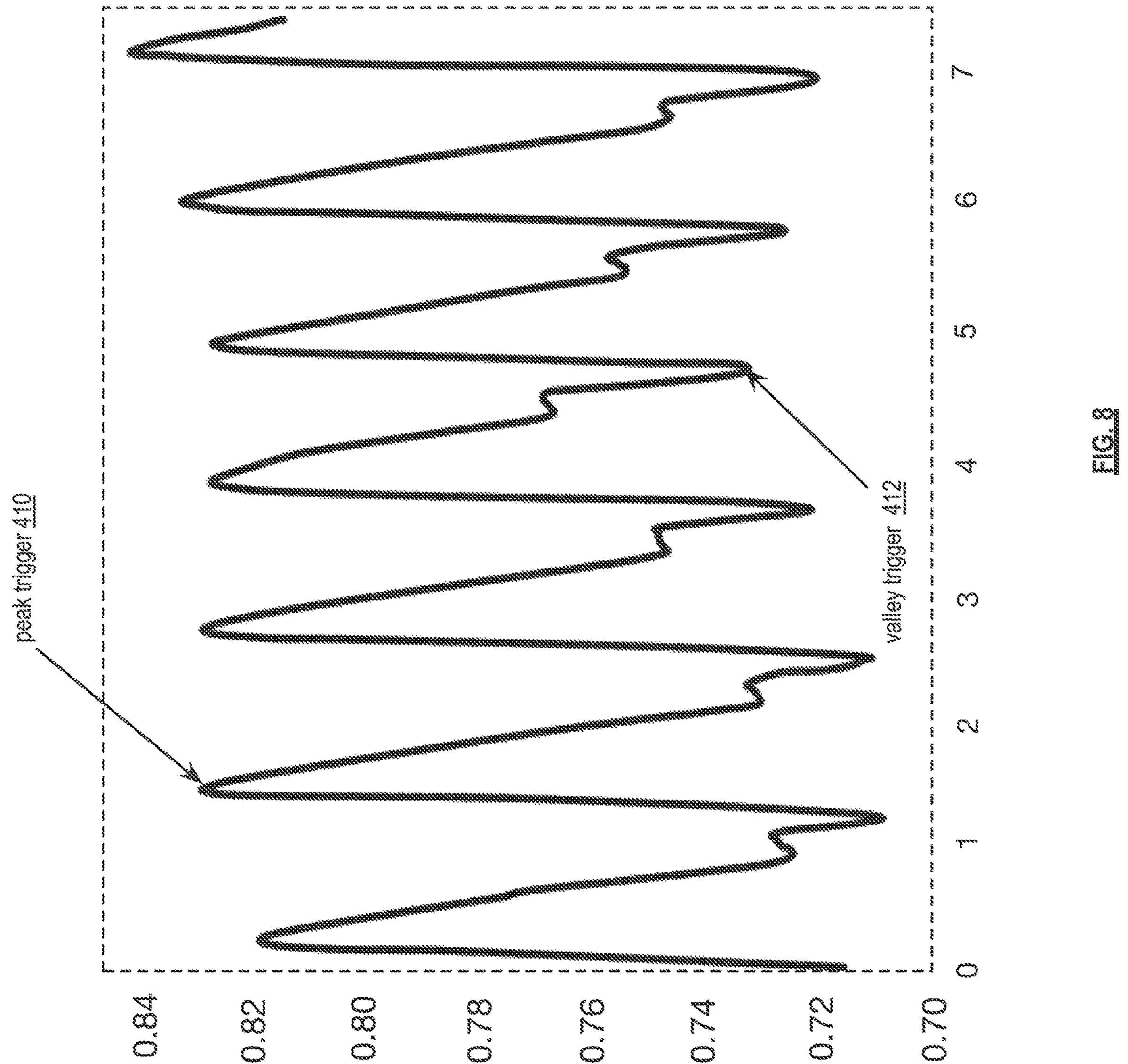
FIG. 8 illustrates the use of a photoplethysmogram (PPG) to determine the peaks and valleys of a cardiac cycle in accordance with the present invention.

FIG. 8 illustrates the use of a photoplethysmogram (PPG) to determine the peaks and valleys of a cardiac cycle. Referring to FIG. 1, photoplethysmography reflects the blood movement in a blood vessel, as it propagates, for example, from the heart to the fingertips through the blood vessels in a wave-like motion. As discussed with reference to FIG. 1, photoplethysmography is an optical measurement technique that uses light radiation to illuminate the tissue, with a combination of propagated, scattered, and transmitted light corresponding with the variation of the blood volume. Example wavelengths for the illumination include green light (530 nm), red light (660 nm), and near infrared (NIR) light (900 nm). In an example, propagated, scattered, and transmitted light can be detected as a photoplethysmography signal.

Referring again to FIG. 1 and accompanying text, a photoplethysmogram (PPG) is an optically obtained plethysmogram that can be used to indicate blood volume changes in a microvascular bed of tissue. A PPG can be obtained, for example, by using a pulse oximeter that illuminates the skin and measures changes in light absorption. In an example, a conventional pulse oximeter can monitor the perfusion of blood to the dermis and subcutaneous tissue of the skin. Referring to FIG. 1 and the associated text as a specific example, a finger pulse oximeter can be used to track blood volume changes.

In an example, during each cardiac cycle, the heart pumps blood to the periphery and though the resultant pressure pulse is attenuated by the time it reaches the skin, the pressure pulse is sufficient to distend the arteries and arterioles in subcutaneous tissue. In a specific example, if a pulse oximeter is attached without substantially compressing the skin, a pressure pulse can also be seen from the venous plexus, as a small secondary peak. In the example, the change in volume caused by the pressure pulse is detected by illuminating the skin with light from a light-emitting diode (LED) allowing measurement of a representation of an amount of light either transmitted or reflected to a photodetector. Each cardiac cycle appears as a peak/valley combination, as seen in FIG. 8. Because blood flow to the skin can be modulated by multiple other physiological systems, the PPG can also be used to monitor breathing, hypovolemia, and other circulatory conditions. Additionally, the shape of the PPG waveform differs from subject to subject and varies with the location and manner in which the pulse oximeter is attached.

As discussed above, PPG can be used to provide heart rate information. However, spectrometer-based systems have a lower sensitivity to light than standard PPG solutions. This is because the received light must be split and detected in narrow or single wavelength ranges, resulting in a tradeoff in resolution per unit area of the sensor and general loss due to a more complex optical path. Illumination sources for spectrometer-based systems necessarily must provide broadband illumination is required, with such illumination sources (such as LEDs) having significantly lower power efficiency compared to narrowband sources used in non-spectrometer-based systems. Accordingly, spectrometer-based systems are not generally a practical replacement as PPG signal samplers. For example, signal-to-noise ratio, sample rate, etc. can be compromised due to any of a lower amount of light reaching the detector, complexity of the detector, and inefficient illumination sources. Some of these deficiencies can be overcome by increasing the illumination power, at the cost of total system power consumption. However, the benefit of using spectrometry for improving the quality of $SpO_2$ extraction is clear.

FIG. 8 illustrates the use of a photoplethysmogram (PPG) based on a narrowband light source providing a strong signal, such as, for example green light, to determine the peaks and valleys of a cardiac cycle. In an example of implementation, green-light heart rate (HR) systems can be used to sample the AC signal of the blood pulsation and used to trigger a spectrometer system only at the green-light based detected peaks and valleys of the PPG signal to provide an HR estimation system. In the example, green-light-based HR estimation systems work in a similar manner to other narrow band PPG systems, except the HR processing pipeline outputs additional triggers to the spectrometer-based system when peaks and valleys are detected. In an example, time-based filtering of the HR processing pipeline by observing the incoming samples can be used to identify peaks and valleys. In a specific example, a first-order derivative can be computed, with zero-crossings of that derivative being the indication of the PPG "peaks and valleys".

In a specific related example of implementation, detected 'peaks' and 'valleys' are used to trigger a spectrometer for a single acquisition. In an example, no oversampling of the PPG is required since the AC amplitude needed to compute $SpO_2$ is readily available. In an example, using the standard, green-based HR measurement system to oversample the PPG signal can reduce the required sample rate of the spectrometer-based system to only 2 samples per heart pulse. Since sample rates of 20-100 are required to properly sample the PPG pulses in a system without a green-light-based HR estimation system, the example system can reduce the required power consumption by, for example, a factor of 10-50.

In an example of implementation and operation, a method for measuring spectrophotometric parameters of skin includes irradiating the skin during a first time window, by a first illumination source, where the first illumination source is configured to provide light over a narrow-predetermined range of optical wavelengths and where the first illumination source is further configured to irradiate light directly onto skin. In an example, the predetermined range of optical wavelengths for the first illumination source is between 495 nm-570 nm. In another example, the first time window is based on a first duty cycle, where a duty cycle is a fraction of time in a given time window during which an illumination source is emitting light. The method continues with a sampling of a received light spectrum by one or more spectrometers during the first time window, where each of the one or more spectrometers includes a plurality of interference filters overlaying one or more optical sensors, wherein each of the one or more spectrometers has a sensing range within a predetermined range of optical wavelengths and is configured to capture light emitted from the skin and where each of the one or more spectrometers is positioned a predetermined distance from the illumination source.

The method continues, by obtaining a photoplethysmogram (PPG) based on the received light spectrum from one or more spectrometers during the first time window, where the PPG includes at least one peak (peak trigger 410) and one valley (valley trigger 412). In response to one or more of the peak trigger 410 or valley trigger 412 of the PPG, the method then continues by irradiating the skin during a second time window, by a second illumination source, where the second illumination source is configured to provide light over a predetermined broad range of optical wavelengths, where the second illumination source is further configured to irradiate light directly onto skin. The method then continues with the sampling of the received light spectrum by the one or more spectrometers during the second time window.

In an example, the one or more spectrometers are positioned a predetermined distance from the first and second illumination source, with the distance to the first illumination source being less than the distance to the second illumination source. In an example, the first illumination source is used primarily to detect the heart rate and the peaks and valleys of the PPG and by placing the first illumination source closer to the one or more spectrometers a strong signal can be received, minimizing the loss of light in skin and tissue while at the same time optimizing the current consumption required to obtain the PPG. In an example, spatially separating the second illumination source from the one or more spectrometers allows the light to travel deeper into skin and picks up a relatively accurate $SpO_2$ level from blood well under the skin. In an example, current consumption needed to provide sufficient intensity to the second illumination source is compensated for by its under-sampling, because the one or more spectrometers only sample the second illumination source at the peaks or valleys of the PPG, based on the available option to activate the second illumination source only for short periods of time at the peaks or valleys of the PPG.

In an example, a processor is used to execute an oxygen saturation ($SO_2$) measurement at one or more valleys in the PPG. In another example the processor is used to execute an oxygen saturation ($SO_2$) measurement at one or more peaks in the PPG. In a specific example, either one of the peaks or valleys are used to measure oxygen saturation ($SO_2$) when using different illumination wavelengths. In yet another specific example, the oxygen saturation ($SpO_2$) measurement is executed based on a ratio of the peak and valley. In a related example, the PPG is used to determine heart rate information based on the peaks and/or valleys determined from the PPG. yet another specific example, the measurement of pulsatile oxygen saturation ($SpO_2$) can require that both the peaks and valleys of the PPG to be used. In a specific related example, multiwavelength measurements can be calculated at known peak and valley locations and used to calculate an AC/DC signal for substantially all relevant wavelengths and serve as an input to the creation of $SO_2$ models.

In a specific example of implementation and operation, at least one peak or valley of a PPG signal is determined based on a computed first-order derivative of the PPG signal. In a related example, a zero-crossing of the computed first-order derivative of the PPG indicates one of a peak or a valley for the PPG signal.

In another specific example of implementation, a device for measuring blood oxygen saturation from skin includes a first illumination source, where the first illumination source is configured to provide light over a predetermined range of optical wavelengths and where the first illumination source is configured to irradiate light directly onto skin. The device also includes at least a second illumination source, where the second illumination source is configured to provide light over a predetermined range of optical wavelengths and the second illumination source is also configured to irradiate light directly onto skin.

In an example, the device includes one or more spectrometers, where each of the one or more spectrometers includes a plurality of interference filters overlaying one or more optical sensors and each of the one or more spectrometers has a sensing range within a predetermined range of optical wavelengths and is configured to capture light emitted from the skin and where each of the one or more spectrometers is positioned a predetermined distance from the first illumination source and the second illumination source.

The device further includes a first processor module, where the first module is adapted to select between the first and second illumination sources to illuminate the skin and a second processor module that is adapted to determine a photoplethysmogram (PPG) when the first illumination source is selected, and the second module is further adapted to select the second illumination source in response to the PPG signal. In a specific example, the PPG signal includes at least one peak or valley, where the second module is adapted to select the second illumination source when the PPG is at a valley and/or at a peak. In a related example, the PPG signal includes a peak and a valley, and the second module is further adapted to select the second illumination source when the PPG is at a peak. In an alternate example, the PPG signal includes a peak and a valley, and the second module is further adapted to select the second source based on a ratio of the peak and valley.

Referring again to FIG. 4, in a specific example of implementation and operation, a method incorporating a spectrometer for measuring $SpO_2$ with two operation modes includes determining, based on the information representative of the first received light spectrum by the one or more processing modules, one or more response peaks for the received light spectrum during a first time window, where a response peak is a momentary high point in the first received light spectrum. The method continues by determining, based on the information representative of the first received light spectrum by the one or more processing modules, one or more response valleys for the received light spectrum during the first time window, where a response valley is a momentary low point in the first received light spectrum and using the one or more response peaks and the one or more response valleys to determine a heart rate.

Figure 9:
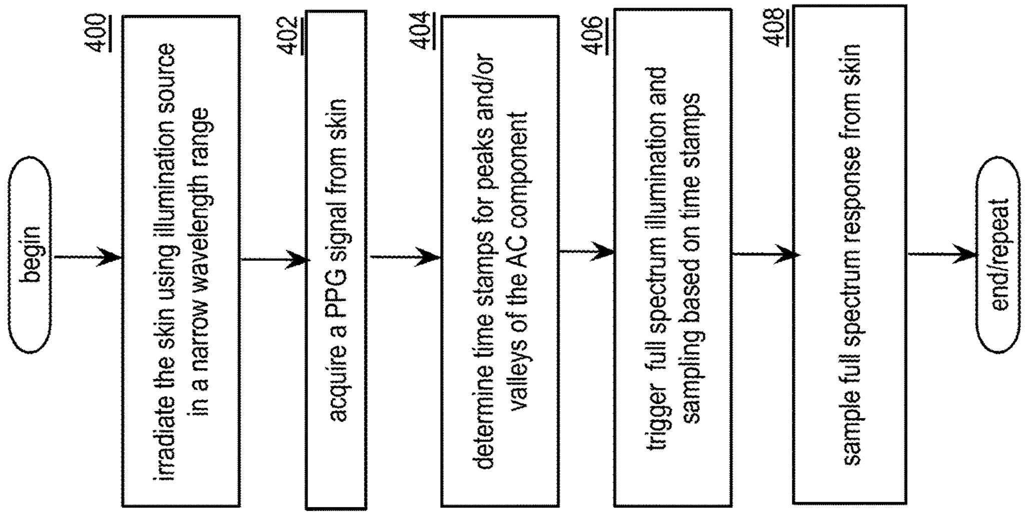
FIG. 9 is a flowchart of a method for incorporating a spectrometer for measuring $SpO_2$ using a photoplethysmogram (PPG) in accordance with the present invention.

FIG. 9 is a flowchart of a method for incorporating a spectrometer for measuring $SpO_2$ using a photoplethysmogram (PPG). The method begins at step 400, with skin being irradiated using an illumination source in a narrow wavelength range. At step 402 the method continues with a photoplethysmogram (PPG) being acquired based on a combination of propagated, scattered and transmitted light from the skin. At step 404 one or more time stamps are determined for the peaks and/or valleys of the PPG signal and at step 406 the time stamps are used to trigger full spectrum illumination from a broad spectrum light source. The method continues at step 408, with the one or more spectrometers sampling the full spectrum response from the illuminated skin.

Figure 10:
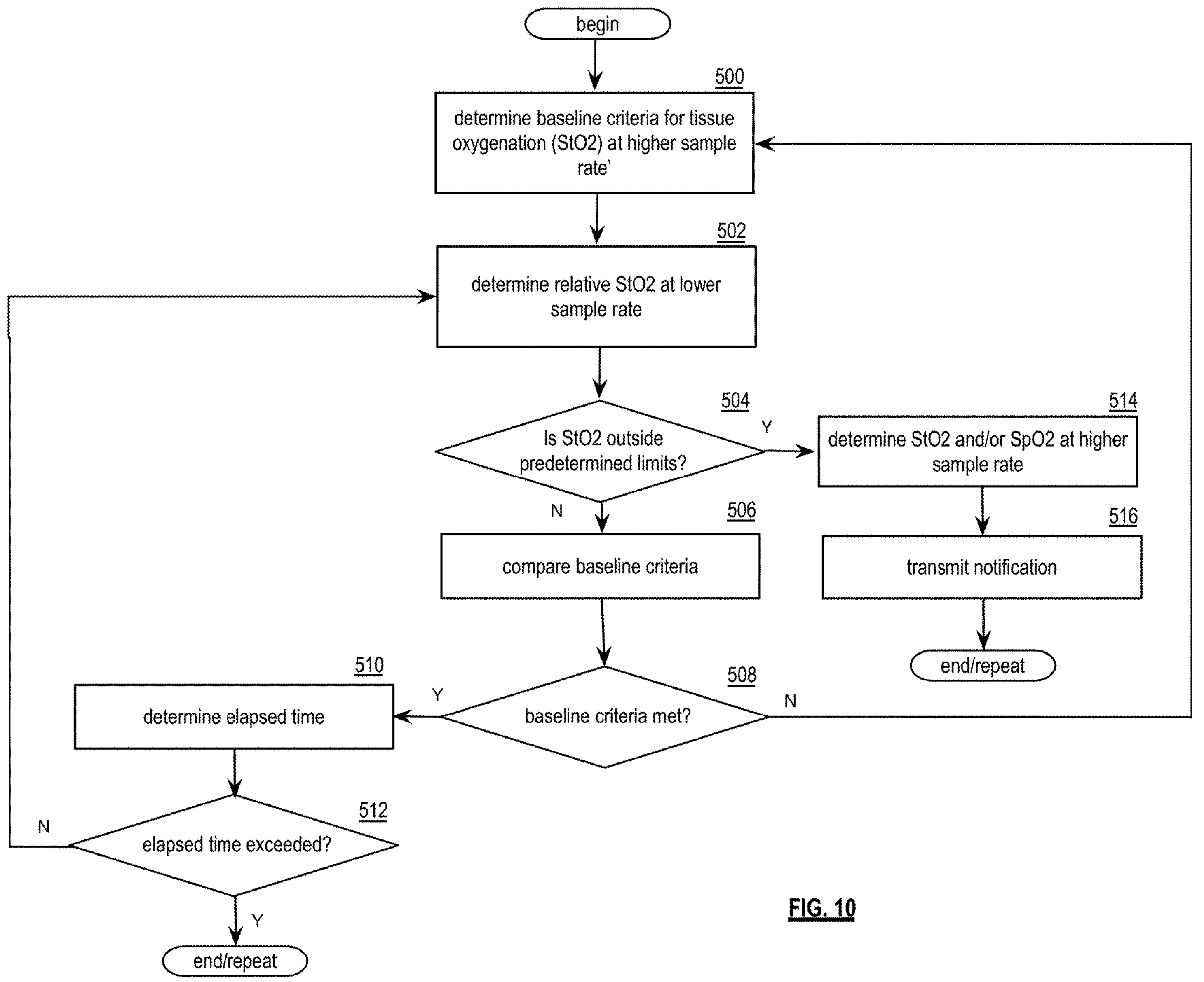
FIG. 10 is a flowchart of an example method for determining oxygen saturation ($StO_2$ and/or $SpO_2$) using a combination of high and low sampling rates in accordance with the present invention.

FIG. 10 is a flowchart of an example method for determining tissue oxygen saturation ($StO_2$) using a combination of high and low sampling rates. The method begins at step 500 with oxygen saturation ($StO_2$ and/or $SpO_2$) being measured at a high sample rate. In an example, the high sample rate measurement is based on a full spectrum illumination source at high current, with the sampling rate selected to provide accurate and precise baseline criteria for $StO_2$. The method continues at step 502, with the sampling of "relative" $StO_2$ at a much lower sample rate. In an example, the low sample rate measurement is based on a narrow-band illumination source at a lower current, with the sampling rate selected to provide a relative $StO_2$. In an alternative example, broad illumination in short pulses can be used to provide a relative $StO_2$. At step 504 the method continues by determining whether the lower sample rate $StO_2$ measurement is outside predetermined limits. For example, the predetermined limits may be defined as a relative change over time in percentage. If a lower sample rate $StO_2$ measurement is outside predetermined limits the method continues at step 514, with the higher sample rate measurement of the $StO_2$ and/or $SpO_2$, followed by an optional step 516, with the notification to a user or automated system that $StO_2$ has exceeded the predetermined limits.

When the $StO_2$ is not outside predetermined limits as determined at step 504, the method continues to step 506 with a comparison to the baseline criteria for $StO_2$ determined at step 500. When the comparison to the baseline criteria is favorable, the method continues at step 510 with a determination whether a predetermined total time has elapsed since the last high sample rate measurement and when the predetermined total time has not elapsed the method continues back to step 502 with the low sample rate measurement being measured. When the comparison to baseline criteria is unfavorable, the method continues back to step 500, with the determination of $StO_2$ at the higher sample rate.

Referring again to FIG. 1, the transmission signals obtained in oximetry have DC components with information related to the blood present in the tissue and veins and of the scattering produced by tissue and bones. The variation of the DC components is slower compared to the variation of the pulsatile (AC) component of a PPG, which can allow measurements at different time intervals for determination of the oxygenation of the blood in the tissue ($StO_2$). In an example of implementation and operation, by using several wavelengths confounding factors can be removed and improve measurement of the blood-related changes.

Figure 11:
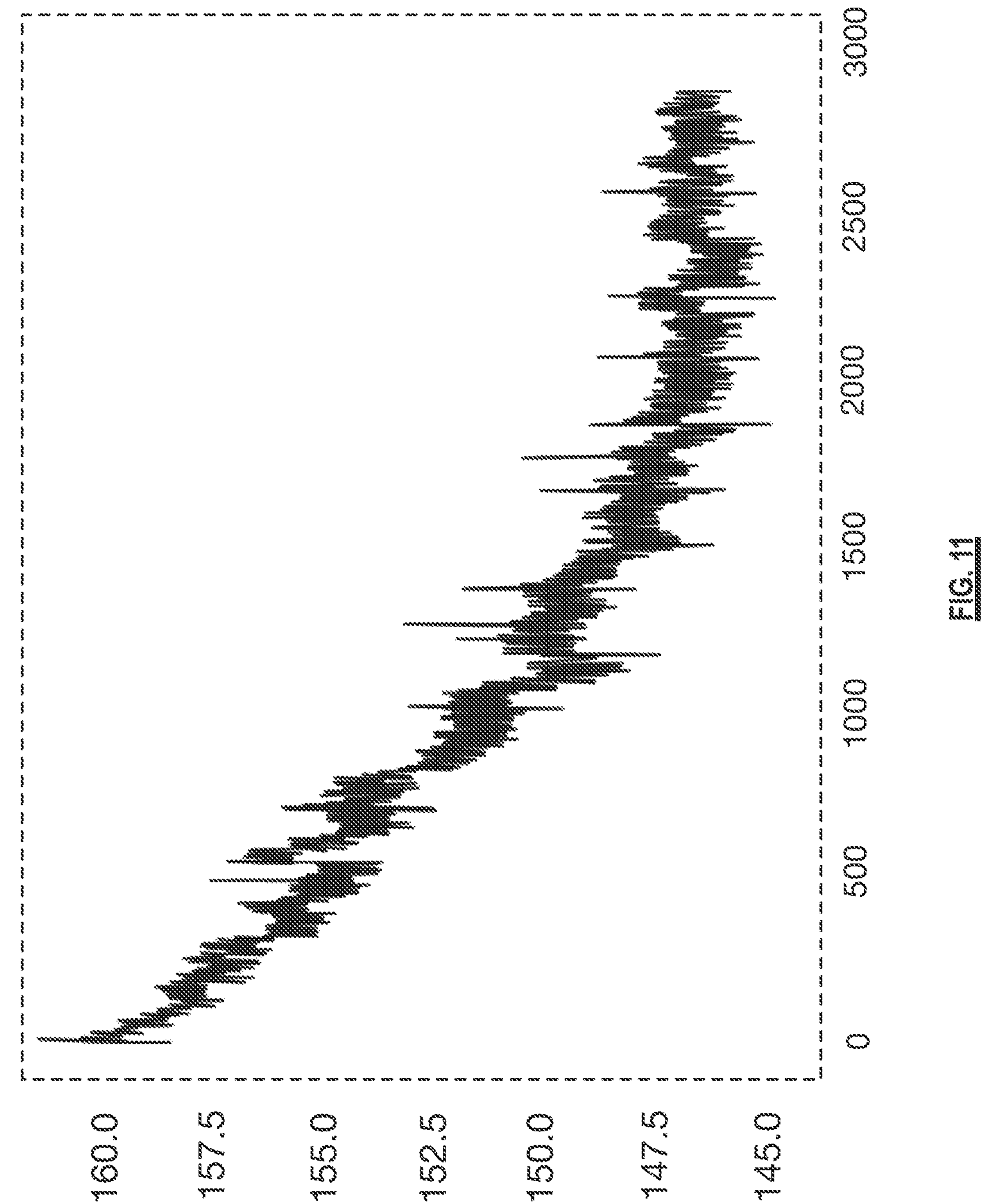
FIG. 11 illustrates the time-varying contribution of the DC components in a representative oximetry system with the abscissa in accordance with the present invention.

FIG. 11 illustrates the time-varying contribution of the DC components in a representative oximetry system with the abscissa (horizontal axis) shown in seconds, with the ordinate (vertical axis) expressed in arbitrary units. Referring to FIG. 3, while the AC component can change rapidly in a time window of a few seconds, while the DC component, as illustrated, changes only over time windows of minutes to hours.

As shown in FIG. 11, the transmitted light intensity varies over time, while the DC component is relatively constant over seconds, therefore, by using a sample rate in the range of 1 Hz this approach could be suitable. Using this method, the results over a time window (such as minutes or hours) can be used to identify trends in the concentration changes.

In a specific example of implementation and operation, the relative tissue oxygen saturation ($StO_2$) can be calculated without using the pulsatory spectrum, but instead by using the time-changes of the DC spectrum. The relative $StO_2$ can thus be calibrated at sparse time intervals with the pulsatory measurement. For example, a first $StO_2$ baseline is determined from the pulsatory signal (high-speed, high-current), e.g. at 100 Hz. The high sampling rate allows accurate and precise measurement of $StO_2$ level and also $SpO_2$ level if desired. In an example, the measurement frequency is then reduced (e.g. 1 Hz), so that static near-infrared spectroscopy (NIRS) spectra are captured and the $StO_2$ relative changes are monitored. In an example, the $StO_2$ level is then measured to determine whether it is within an acceptable range and/or if the rate of change is within acceptable limits. In an example, if at least one of the conditions is unfavorable, the system can then execute a new high sampling measurement to determine new $StO_2$ baseline and the $SpO_2$ levels. If at least one of them is outside of acceptable limits a signal can be sent to a user or automated system.

If on the other hand the $StO_2$ criteria are favorable, criteria for a new accurate $StO_2$ baseline measurement are verified (for example, every hour). If the criteria are verified, the system can begin again at baseline determination, if not verified, the system can determine if the total time (8 hours for example) has elapsed and repeat the relative $StO_2$ measurement if the total time has not been reached.

In a specific example of implementation and operation, a device for measuring optical response from skin includes a first illumination source, wherein the first illumination source is configured to provide light over a predetermined range of optical wavelengths and the first illumination source is further configured to irradiate light directly onto skin. The device includes a second illumination source, where the second illumination source is configured to provide light over a predetermined range of optical wavelengths and the second illumination source is also configured to irradiate light directly onto skin. The device includes one or more spectrometers, where each of the one or more spectrometers includes a plurality of interference filters overlaying one or more optical sensors, where each of the one or more spectrometers has a sensing range within a predetermined range of optical wavelengths and is configured to capture light emitted from the skin, where each of the one or more spectrometers is positioned a predetermined distance from the first illumination source and the second illumination source.

The device includes a first processor module, where the first processor module is adapted to sample a received light spectrum from the one or more spectrometers at a first and second sample rate and a second processor module the second processor module is adapted to select between the first sample rate and the second sample rate, where the first sample rate is higher than the second sample rate.

In another example of operation, a method for measuring spectrophotometric parameters of a body area begins by irradiating the body area during a first time window, by a first illumination source, where the first illumination source is configured to provide light over a predetermined range of optical wavelengths and the first illumination source is further configured to irradiate light directly onto skin. The method continues by sampling a received light spectrum by one or more spectrometers during some portion of the first time window, where each of the one or more spectrometers includes a plurality of interference filters overlaying one or more optical sensors, and each of the one or more spectrometers has a sensing range within a predetermined range of optical wavelengths and is configured to capture light emitted from the skin and where each of the one or more spectrometers is positioned a predetermined distance from at least one illumination source of the one or more illumination sources. The method continues with obtaining a photoplethysmogram (PPG) based on the received light spectrum from the one or more spectrometers during the first time window, where the PPG includes at least one peak and one valley.

In response to the PPG, the method continues by irradiating the skin during a second time window, by a second illumination source, where the second illumination source is configured to provide light over a predetermined range of optical wavelengths and the second illumination source is further configured to irradiate light directly onto skin. The method then continues by sampling a received light spectrum by the one or more spectrometers during the second time window.

As may be used herein, the terms “substantially” and “approximately” provide industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) “configured to”, “operably coupled to”, “coupled to”, and/or “coupling” includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as “coupled to”.

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A method for measuring body parameters comprises:

irradiating a body area during a first time window using a first illumination source, wherein the first illumination source is configured to provide light over a predetermined range of optical wavelengths;

sampling, by a first plurality of spectral sensors, a first received light spectrum for the body area, wherein each spectral sensor of the first plurality of spectral sensors includes a spectral filter overlaying an optical sensor, wherein each spectral sensor has a sensing range within a predetermined range of optical wavelengths, wherein the sensing range for the first plurality of spectral sensors includes a spectrum of wavelengths, wherein each spectral sensor is positioned a predetermined distance from the first illumination source;

outputting, via one or more interfaces, information representative of the first received light spectrum to one or more processing modules;

irradiating the body area during a second time window using a second illumination source, wherein the second illumination source is configured to provide light over a predetermined range of optical wavelengths;

sampling, by a second plurality of spectral sensors, a second received light spectrum for the body area, wherein each spectral sensor of the second plurality of spectral sensors includes a spectral filter overlaying an optical sensor, wherein each spectral sensor has a sensing range within a predetermined range of optical wavelengths, wherein the sensing range for the second plurality of spectral sensors includes a spectrum of wavelengths; and outputting, via one or more interfaces, information representative of the second received light spectrum to the one or more processing modules.

2. The method of claim 1, wherein the predetermined range of optical wavelengths for the first illumination source is between 930 nm and 950 nm.

3. The method of claim 1, wherein the first time window is based on a first duty cycle, wherein a duty cycle is a fraction of time in a time window during which an illumination source is emitting light.

4. The method of claim 1, further comprising:

limiting, by one or modules of the one or more processing modules, the sampling of the first received light spectrum to spectral sensors with a sensing range within optical wavelengths associated with the first illumination source.

5. The method of claim 1, wherein the first time window and the second time window partially overlap.

6. The method of claim 1, wherein the first time window and the second time window do not overlap.

7. The method of claim 1, wherein the predetermined range of optical wavelengths for the second illumination source is between 640 nm and 680 nm.

8. The method of claim 1, wherein the first time window is based on a first duty cycle, wherein the second time window is based on a second duty cycle.

9. The method of claim 1, further comprising:

limiting, by the one or more processing modules, the sampling of the second received light spectrum for the body area during the second time window to spectral sensors with a sensing range within optical wavelengths associated with the second illumination source.

10. The method of claim 1, further comprising:

irradiating, by a third illumination source, the body area during a third time window, wherein the third illumination source is configured to provide light over a predetermined range of optical wavelengths; and sampling, by a third plurality of spectral sensors, a third received light spectrum for the body area, wherein each spectral sensor of the third plurality of spectral sensors includes a spectral filter overlaying an optical sensor, wherein each spectral sensor has a sensing range within a predetermined range of optical wavelengths, wherein the sensing range for the second plurality of spectral sensors includes a spectrum of wavelengths; and outputting, via one or more interfaces, information representative of the third received light spectrum to the one or more processing modules.

11. The method of claim 10, wherein the predetermined range of optical wavelengths for the third illumination source is wider than the predetermined range of optical wavelengths for either of the first illumination source or the second illumination source.

12. The method of claim 10, wherein the first time window is based on a first duty cycle, wherein the second time window is based on a second duty cycle, wherein the third time window is based on a third duty cycle, wherein the third time window is shorter than either of the first time window or the second time window.

13. The method of claim 10, wherein the predetermined range of optical wavelengths for the third illumination source is between 400 nm and 1000 nm.

14. The method of claim 1, further comprising:

determining, based on the information representative of the first received light spectrum by the one or more processing modules, one or more response peaks for the received light spectrum during the first time window, wherein a response peak is a momentary high point in the first received light spectrum;

determining, based on the information representative of the first received light spectrum by the one or more processing modules, one or more response valleys for the received light spectrum during the first time window, wherein a response valley is a momentary low point in the first received light spectrum; and using the one or more response peaks and the one or more response valleys to determine a heart rate.

15. The method of claim 14, wherein the one or more response peaks are determined using a first-order derivative from the information representative of the first received light spectrum during the first time window.

16. The method of claim 14, wherein the predetermined range of optical wavelengths for the first illumination source is between 495 nm and 570 nm.

17. A device for measuring optical response from skin comprises:

a first illumination source, wherein the first illumination source is configured to provide light over a predetermined range of optical wavelengths, wherein the first illumination source is further configured to irradiate light directly onto the skin;

a second illumination source, wherein the second illumination source is configured to provide light over a predetermined range of optical wavelengths, wherein the second illumination source is also configured to irradiate light directly onto the skin;

a plurality of spectral sensors, wherein each spectral sensor of the plurality of spectral sensors includes a spectral filter overlaying an optical sensor, wherein each spectral sensor has a sensing range within a predetermined range of optical wavelengths, wherein the sensing range for the plurality of spectral sensors includes a spectrum of wavelengths, wherein each spectral sensor is positioned a predetermined distance from the first illumination source and the second illumination source;

a first module of the one or more processors, adapted to select between the first and second illumination sources; and a second module of one or more processors adapted to produce a spectral response from the plurality of spectral sensors.

18. The device of claim 17, wherein the predetermined range of optical wavelengths for the second illumination source is between 640 nm and 680 nm.

19. The device of claim 17, further comprising:

a third illumination source configured to provide light over a predetermined range of optical wavelengths, wherein the third illumination source is configured to irradiate light directly onto the skin.

20. The device of claim 19, wherein the predetermined range of optical wavelengths for the third illumination source is wider than the predetermined range of optical wavelengths for either of the first illumination source or the second illumination source.

21. The device of claim 20, wherein the predetermined range of optical wavelengths for the third illumination source is between 400 nm and 1000 nm.

22. A device for measuring optical response from skin, the device comprising:

a first illumination source, wherein the first illumination source is configured to provide light over a predetermined range of optical wavelengths, wherein the first illumination source is further configured to irradiate light onto skin;

a second illumination source, wherein the second illumination source is configured to provide light over a predetermined range of optical wavelengths, wherein the second illumination source is further configured to irradiate light onto skin;

a third illumination source, wherein the third illumination source is configured to provide light over a predetermined range of optical wavelengths, wherein the third illumination source is further configured to irradiate light onto skin;

one or more spectrometers, wherein each of the one or more spectrometers includes a plurality of interference filters overlaying one or more optical sensors, wherein each of the one or more spectrometers has a sensing range within a predetermined range of optical wavelengths and is configured to capture light emitted from the skin, further wherein each of the one or more spectrometers is positioned a predetermined distance from the first illumination source, the second illumination source and the third illumination source, wherein the one or more spectrometers are adapted to output, via one or more interfaces, information representative of a received light spectrum to one or more processors;

a first module of the one or more processors, wherein the first module is adapted to select between one or more of the first, second and third illumination source to illuminate the skin; and a second module of one or more processors, wherein the second module is adapted to produce a spectral response for at least a portion of one spectrometer of the one or more spectrometers.

* * * * *